(12) United States Patent
Van Beek

(10) Patent No.: US 8,158,166 B2
(45) Date of Patent: *Apr. 17, 2012

(54) ENHANCED ANTIMICROBIAL ACTIVITY COMPOSITIONS OF BLENDS OF PLANT ESSENTIAL OILS

(76) Inventor: Ronald R. Van Beek, Orange City, IA (US)

( * ) Notice: Subject to any disclaimer, the term of this patent is extended or adjusted under 35 U.S.C. 154(b) by 85 days.

This patent is subject to a terminal disclaimer.

(21) Appl. No.: 12/758,400

(22) Filed: Apr. 12, 2010

(65) Prior Publication Data

US 2010/0196494 A1    Aug. 5, 2010

Related U.S. Application Data

(63) Continuation-in-part of application No. 12/426,622, filed on Apr. 20, 2009, now abandoned.

(60) Provisional application No. 61/053,216, filed on May 14, 2008.

(51) Int. Cl.
*A61K 36/00* (2006.01)
*A61K 36/53* (2006.01)
*A61K 36/54* (2006.01)
*A61K 9/16* (2006.01)

(52) U.S. Cl. ......... 424/725; 424/745; 424/739; 424/490

(58) Field of Classification Search .................. None
See application file for complete search history.

(56) References Cited

U.S. PATENT DOCUMENTS

| 3,699,221 | A | | 10/1972 | Schole et al. |
| 3,957,964 | A | | 5/1976 | Grimm, III |
| 5,190,748 | A | * | 3/1993 | Bachynsky et al. ......... 424/78.08 |
| 5,756,073 | A | * | 5/1998 | Miller et al. .................... 424/49 |
| 5,837,222 | A | | 11/1998 | Cloonan et al. |
| 2005/0013883 | A1 | | 1/2005 | Becker |
| 2005/0014730 | A1 | | 1/2005 | Carlson et al. |
| 2005/0196359 | A1 | | 9/2005 | D'Amelio, Sr. et al. |
| 2006/0275222 | A1 | | 12/2006 | James Dodds et al. |
| 2007/0197658 | A1 | | 8/2007 | David et al. |
| 2008/0063693 | A1 | | 3/2008 | Cook et al. |

FOREIGN PATENT DOCUMENTS

| DE | 10005886 A1 | 8/2001 |
| DE | 202007003020 U1 | 7/2007 |
| WO | 9600056 A1 | 1/1996 |
| WO | 9637210 A2 | 11/1996 |
| WO | 9966796 A1 | 12/1999 |
| WO | 2004076680 A2 | 9/2004 |

OTHER PUBLICATIONS

Hersch-Martinez et al, Antibacterial effects of commercial essential oils over locally prevalent pathogenic strains in Mexico, Fitoterapia 76 (2005) 453-457.*
Helander et al, Polyethyleneimine is an effective permeabilizer of Gram-negative bacteria, Microbiology (1997), 143, 3193-3199.*
Faleiro, Leonor et al., "Antibacterial and Antioxidant Activities of Essential Oils Isolated from *Thymbra capitata* L. (Cav.) and *Origanum vulgare* L." J. Agric. Food Chem. 2005, 53, pp. 8162-8168.
Hammer, K.A. et al., "Antimicrobial activity of essential oils and other plant extracts", Journal of Applied Microbiology, 1999, 86, pp. 985-990.
Daferera et al., "The effectiveness of plant essential oils on the growth of *Botrytis cinerea, Fusarium* sp., and *Clavibacter michiganensis* subsp. *michiganensis*", Crop Protection (2003), 22(1):39-44.
Helander et al., "Polyethyleneimine is an effective permeabilizer of Gram-negative bacteria", Microbiology (1997), 143:3193-3199.
Vareltizis et al., "Antimicrobial Effects of Sodium Tripoyphosphate Against Bacteria Attached to the Surface of Chicken Carcasses", Lebensmittel-Wissenschaft und-technologie, 30(7):665-669 (1997).
Antibiotics Chemotherapy, "Coping with resistance in the community", International Society of Chemotheraphy, Dec. 2003, vol. 7, No. 3, 16 pages.

* cited by examiner

*Primary Examiner* — Qiuwen Mi
(74) *Attorney, Agent, or Firm* — McKee, Voorhees & Sease, P.L.C.

(57) ABSTRACT

Antimicrobial compositions based on a combination or blend of plant essential oils is of enhanced antimicrobial effectiveness; by adding to the combination of at least two plant essential oils, and preferably adds a small but antimicrobial enhancing effective amount of an enhancer selected from the group consisting of polyionic organic enhancers and polyionic inorganic enhancers. One preferred blended oil composition is a mixture of plant essential oils wherein at least one of the oils is oregano oil. The oil blend is used as a major component in the finished product anti-microbial.

4 Claims, No Drawings

ENHANCED ANTIMICROBIAL ACTIVITY COMPOSITIONS OF BLENDS OF PLANT ESSENTIAL OILS

CROSS-REFERENCE TO RELATED APPLICATIONS

This Continuation-in-part application claims priority under 35 U.S.C. §120 of application Ser. No. 12/426,622 filed Apr. 20, 2009 now abandoned, and under 35 U.S.C. §119(e) to provisional application Ser. No. 61/053,216 filed May 14, 2008, each of which are herein incorporated by reference in their entirety.

FIELD OF THE INVENTION

This invention relates to methods and compositions using plant essential oil blends as antimicrobials.

BACKGROUND OF THE INVENTION

It is known in the art that plant essential oils, that is oils derived from plants by distillation, expression or extraction may have antimicrobial activity when exposed to bacterial cells, yeast and mold. Consumer acceptance of these essential oils is high because they usually have the pleasant fragrance of the plant from which they were extracted. When used for animal use, the animals do not commonly shy away from them because again, they have the odor of plants from which they were derived, and such odors are not unfamiliar to many animals.

Essential oils mixed with carriers have a lot of potential veterinary and human uses. For example in the veterinary world they may be used as teat dips, or disinfecting topicals such as for skin ulcers, for shampoos, for topical gels and creams, for anti-fungals, and even can be taken internally for use in the GI tract, such as for scours products. These final or finished products are collectively referred to herein as "finished products".

There is a continuing need for increasing the cellular uptake of plant essential oils in order to enhance their antibacterial effect. Some researchers have theorized that plant essential oils soften the walls of the bacteria then permeate them thus causing an enhanced anti-bacterial effect. (see, Vaara, "Agents That Increase the Permeability of the Outer Membrane", *Microbiological Reviews,* September 1992, Vol. 56(3); and Johnson U.S. Pat. No. 6,319,958 that teaches addition of at least one sesquiterpenoid to advance the antimicrobial effect of antimicrobial compounds.

In the ever increasing efforts to enhance antimicrobial effectiveness Applicant has now discovered that a combination of plant essential oils (blends) provides increased enhancement; and moreover the combination of oils may be used with other known additional enhancers to even further maximize effectiveness of many disinfecting topicals.

Accordingly it is an object of the present invention to provide plant essential oil-derived antimicrobial compositions, that use a combination of essential oils, and in some cases added enhancers are also used with the oil blends, to achieve a maximized antimicrobial effect.

It is also an object of this invention to prepare a variety of different antimicrobial compositions based on the above discovery that are useful for veterinary or human use.

The method or means of accomplishing at least the above objectives will become apparent from the detailed description of the invention which follows hereinafter.

BRIEF SUMMARY OF THE INVENTION

Antimicrobial compositions based on a combination of plant essential oils are of enhanced antimicrobial effectiveness and are prepared by adding a blend of at least two plant essential oils preferably with a small but antimicrobial enhancing effective amount of an additional enhancer selected from the group consisting of polyionic organic enhancers and polyionic inorganic enhancers to a disinfecting composition such as a teat dip or scours treatment. One preferred combination or blend is a mixture of plant essential oils wherein at least one of the oils is oregano oil.

DETAILED DESCRIPTION OF THE PREFERRED EMBODIMENT

This invention relates to antimicrobial compositions derived from plant essential oils, more importantly a combination of essential oils to enhance antimicrobial effectiveness. The essential oil component as a concentrate may be from 40% to 95% by weight oils, but is preferably from 50% to 90% by weight of a combination of essential oils. The balance is usually a known organic acid anti-microbial such as citric acid, butyric acid, fumaric acid, lactic acid and acetic acid. The most preferred essential oils being a 1 to 1 by weight mix of at least two different essential oils, with one of them being oregano oil. As a major component as herein defined means of the total concentrate at least 40% by weight.

Essential oils are volatile aromatic oils which may be synthetic or may be derived from plants by distillation, expression or extraction, and which usually carry the odor or flavor of the plant from which they are obtained. In the combination compositions of this invention, antiseptic activity is provided by essential oils. Some of these essential oils also act as flavoring agents. Besides oregano oil and thymol, the essential oils of this invention may include but are not limited to menthol, methyl salicylate (wintergreen oil), eucalyptol, carvacrol, camphor, chamomile, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, and clove oil.

In embodiments of the invention wherein organic phenolic compounds are obtained from plant oil extracts, the oil is preferably extracted from a member of the *Labiatae* (also called *Lamiaceae*) or *Verbenaceae* family. Plants in the family *Labiatae* or *Verbenaceae* include hybrids of plants produced from individual plants in those two families.

The common name for members of the *Labiatae* family, a large family of mostly annual or perennial herbs, is the "mint family." The mint family is classified in the division Magnoliphyta, class Magnoliopsida, and order Lamiales. The *Labiatae* family includes about 200 genera, such as *Salvia, Rosmarinus, Mentha, Ocimum, Thymus, Marrubium, Monarda, Trichostema, Teucrium, Hyptis, Physostegia, Lamium, Stachys, Scutellaria* and *Lycopus.*

Plants which are preferably used for extraction of organic phenolic compounds include, but are not limited to, *Ocimum* spp., *Saturea* spp., *Monarda* spp, *Origanum* spp, *Thymus* spp., *Mentha* spp., *Nepeta* spp., *Teucrium gnaphalodes, Teucrium polium, Teucrim divaricatum, Teucrim kotschyanum, Micromeria myrifolia, Calamintha nepeta, Rosmarinus officinalis, Myrtus communis, Acinos suaveolens, Dictamnus albus, Micromeria fruticosa, Cunila origanoides, Mosla Japonoica Maxymowitz, Pycnanthemum nudum, Micromeria*

*Juliana, Piper betel, Trachyspermum ammi, Lippia graveolens Escholcia splendens,* and *Cedrelopsis grevei,* as well as others.

In a preferred composition, the oil is extracted from *Esholtia splendens, Cedrelopsis grevei, Lippia graveolens* or a plant of the species *Nepeta,* including but not limited to *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinii, Nepeta nepetella, Nepeta sibthorpii, Nepeta subsessilis* and *Nepeta tuberosa.*

Most preferably, the oil is extracted from a hybrid plant produced from crossing *Nepeta racemosa, Esholtia splendens, Cedrelopsis grevei,* and *Lippia graveolens.*

Plants of the *Labiatae* and *Verbenacea* families are found throughout the world and are relatively easy to cultivate. To cultivate the plants, seeds, preferably those of plants that are expected to yield a high percentage (e.g., at least about 70 wt %, more preferably at least about 80 wt %), of organic phenolic compounds, are planted in fine loose soil, preferably in a sub-tropical climate. Hybrid seeds having a high percentage of organic phenolic compounds can be produced by known techniques. Crossing *Nepeta racemosa, Esholtia splendens, Cedrelopsis grevei,* and *Lippia graveolens* produces one such hybrid that is a preferred source of the organic phenolic compounds. The seeds are then cultivated using known agricultural techniques, such as watering, and artificial fertilizing. Most preferably, the plants are cultivated and grown without the use of any synthetic pesticides.

Because the leaves contain a high amount of oil upon blossoming, it is preferred that the plants be harvested soon after the plants begin to blossom. Preferably, the plants are harvested within 24 hours after blossoming, more preferably within 12 hours after blossoming. Most preferably, harvesting is undertaken early in the morning or late in the evening hours (after blossoming begins) when the leaves are not exposed to the sun.

Because the majority of the oil is found in the leaves and blossoms of the plant, it is preferred that only the leaves and blossoms be utilized in the extraction process. Use of other parts of the plant may increase impurities and decrease yield, but may be utilized.

Thymol, also known by the chemical formula 5-methyl-2-(1-methylethyl) phenol, is obtained from the essential oil of *Thymus vulgaris Labiatae* and *Monarda punctata Labiatae.* Thymol is a white crystalline powder with an aromatic odor and taste and is soluble in organic solvents but only slightly soluble in deionized water. Thymol along with oregano oil are preferred for at least one of the combination of essential oils Menthol is isolated principally from the oil of Mentha arvensis. In its commercial form, menthol is available as L-menthol crystals obtained from a process involving cooling of the oil. Fractional distillation of peppermint oil which usually contains from about 40% to about 65% menthol represent another important source of menthol. Synthetic sources of L-menthol are also available.

Eucalyptol, another essential oil with antiseptic properties, is derived from the eucalyptus tree. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels.

Methyl salicylate is the main ingredient in many essential oils, constituting about 99% of oil of wintergreen (*Gaultheria procumbens*) and sweet birch (*Betula lento*). Methyl salicylate, which has a distinctive refreshing aroma, is used widely in mouthwashes, chewing gums and other oral and pharmaceutical preparations.

In the most preferred compositions of the present invention it is preferred that at least one of the essential oils have as their active ingredient a combination of thymol and carvacrol. The most preferred is oregano oil.

One very satisfactory oil blend is 47.5% by weight oregano oil, 23.75% by weight cinnamon bark oil, and 23.75% by weight clove oil and 5% capsicum oil resin. Another oil blend which may also be used is: 46% by weight oregano, 22% cinnamon bark, 22% clove, 5% nerolidol and 5% capsicum.

A third blend formulation is 30% oregano, 30% cinnamon bark, 30% clove, 5% nerolidol and 5% capsicum.

A fourth blend formulation is 36.20% oregano, 18% cinnamon bark, 17% clove, 4% nerolidol, 0.8% oleoresin capsicum, 4% cranberry, 6.60% geranium, 6.67% patchouli, and 6.67% tea tree.

A fifth blend formulation is 33% regular oregano, 33.34% clove, and 33.34 cinnamon.

A sixth blend formulation is 95% rosemary oil and 5% nerolidol.

The essential oils can be mixed in a variety of physical formats, with one preferred one being so called beads. Bead format is from 0.5% to 50% of a combination of oils or pure oil added to a mixture of alginate, shellac and seaweed carriers to provide a carrier bead with the oil or oils. This allows for a convenient and easy subsequent processing. The beading process is known and can be accomplished by a variety of manufacturers.

Products based on essential oils, such as those containing organic phenolic compounds, tend to be absorbed at a level greater than 90% in the small intestines. Therefore, most of the activity of such products tends to be localized in the stomach and/or small intestine. However, there are many microbial infections that occupy portions of the gastrointestinal tract beyond the small intestine. Therefore, it may be desirable to extend the activity of the combination essential oil based product into the large intestine.

Microencapsulation is one method that can help extend the-activity of the antimicrobial composition throughout the entire gastro-intestinal tract (GIT). Microencapsulation is a micro-packaging technique which involves the coating of small particles of solids, liquid droplets, or dispersion of solids, within liquids. Microencapsulated antimicrobial compound may be used to treat infections located in the end of the small intestines (e.g., jejunum and/or ileum) and beginning of the large intestines (e.g., ascending colon and transverse colon). The microencapsulation prevents release of the active ingredients in the stomach or in the beginning of the small intestines (e.g., duodenum). If the antimicrobial compound is not microencapsulated, the acidic environment of the stomach will tend to break the association between the antimicrobial compound and most carriers in the pharmaceutical composition (such as dextrose, starch, etc.) and thereby activate the antimicrobial compound in the stomach.

For example, a microencapsulated form of the antimicrobial compositions may be used to treat *Cryptosporidia* spp. infections and/or chronic enteritis in humans; *Cryptosporidia* infections in animals, *Lawsonia intracellularis* and *Treponema hyodesynteriae* infections in pigs, and others.

One example of a microencapsulation process includes encapsulating the antimicrobial composition in a multi walled capsule such that the layers of the wall dissolve as the capsule travels through the gastrointestinal tract. Thus, the components that make up each layer of the capsule wall are chosen based on the conditions in the specific region of the gastrointestinal tract in which they are desired to dissolve. For example, the pH along the gastrointestinal tract (GIT) varies: in the stomach, the pH is between 2 and 5; in the duodenum, 4 and 6; jejunum, 4 and 6; ileum, 6.5 and 7.5; caecum 5.5 and 6.5; colon, 6.5 and 7; and rectum, 6.5 and 7. Therefore, the components of the wall layers may differ depending on what type of an ailment is to be treated, or its location, and whether the final formulation is meant to treat humans or animals. Each layer of the wall may also contain the composition of the invention so that upon dissolution of that wall layer, it can be released to effectuate treatment of the ailment.

Suitable coating matrices include fatty acids, waxes, sugars, and shellac.

Encapsulation techniques are known. An example of one encapsulation technique (called fluidized bed coating) is provided below. In a fluidized bed, a suspension of solid particles is transformed into a fluid-like state by an upward gas flow through the system. Because of the intensive heat and mass transfer, fluidized bed reactors are widely used, e.g. in chemical industry for solid-catalyzed gas-phase reactions. To maximize the yield of such reactors, liquid reactants can locally be injected into the fluidized bed. The injected liquid reactants penetrate the fluidized bed and evaporate. For design purposes and the achievement of optimal operating conditions, the spatial distribution of the concentration of components and temperature has to be predicted.

Fluidized bed coating can be used to encapsulate the antimicrobial compound in a coating material which includes ethyl cellulose and plant oil. First, the antimicrobial compound described is combined in the fluid bed mixer with the ingredients to form a powder, such as the ingredients shown in the table below.

While the above disclosure has been emphasizing blends of at least two oils with at least one being oregano, multi-oil blends with at least one being oregano also work.

CONCENTRATE EXAMPLES

Three especially preferred oil blend formulas include the following:

| 1$^{st}$ Oil Blend Formula: | |
|---|---|
| Base Formula* | 33.34% |
| Regular Oregano Oil | 33.34% |
| Rosemary Oil | 11.11% |
| Licorice Powder | 11.11% |
| Cinnamon Bark | 11.11% |
| | 100% |

| 2$^{nd}$ Oil Blend Formula: | |
|---|---|
| Base Formula* | 33.34% |
| Regular Oregano Oil | 33.34% |
| Rosemary Oil | 11.11% |
| Chamomile Oil | 11.11% |
| Peppermint Oil (high menthol content) | 11.11% |
| | 100% |

| 3$^{rd}$ Oil Blend Formula: | |
|---|---|
| Base Formula* | 33.34% |
| Regular Oregano Oil | 33.34% |
| Cinnamon Bark Oil | 11.11% |
| Rosemary Oil | 11.11% |
| Peppermint Oil (high menthol content) | 11.11% |
| | 100% |

These may be used with additional enhancers and other ingredients to form finished products.
*Base Formula as used here includes 33% Geranium oil, 33.34% Patchouli and 33.34 Tea Tree oil.

SCOURS FINISHED PRODUCT EXAMPLE

Two scours treating products were made, each containing combinations of essential oils, as listed below in the finished product. Product A contained sodium polyphosphate inorganic enhancer. Product B contained three enhancers Nerolidol, PEI, and sodium polyphosphate.

| A Ingredient | Percentage | B Ingredient | Percentage |
|---|---|---|---|
| Purified Water | 44.60% | Purified Water | 39.60% |
| Activated Charcoal | 10.00% | Activated Charcoal | 10.00% |
| Regular Oregano Oil | 7.50% | Regular Oregano Oil | 7.20% |
| Cinnamon Bark Oil | 3.25% | Cinnamon Bark Oil | 7.20% |
| Redistilled Clove Leaf Oil | 2.75% | Redistilled Clove Leaf Oil | 3.60% |
| Nerolidol | 0.50% | Nerolidol | 1.00% |
| Capsicum Oleoresin | 0.75% | PEI | 0.50% |
| Cranberry Extract | 0.25% | Sodium Polyphosphate | 0.50% |
| Dextrose | 5.00% | Dextrose | 5.00% |
| Agro-Pect | 5.00% | Agro-Pect | 5.00% |
| Arabic Gum | 2.50% | Arabic Gum | 2.50% |
| Glycine | 2.50% | Glycine | 2.50% |
| Psylium Seed Hulls | 2.50% | Psylium Seed Hulls | 2.50% |
| Betaine Hydrochloride | 2.00% | Betaine Hydrochloride | 2.00% |
| Seaweed Meal---Nori Flakes | 2.00% | Seaweed Meal---Nori Flakes | 2.00% |
| Citric Acid | 1.50% | Citric Acid | 1.50% |
| Sodium Chloride (Extra Fine) Salt | 1.50% | Sodium Chloride (Extra Fine) Salt | 1.50% |
| Potassium Chloride (Muriate of Potash) | 1.50% | Potassium Chloride (Muriate of Potash) | 1.50% |
| Magnesium Chloride | 1.00% | Magnesium Chloride | 1.00% |
| Citricidal | 1.00% | Citricidal | 1.00% |
| Ascorbic Acid | 1.00% | Ascorbic Acid | 1.00% |
| Zinc Oxide | 1.00% | Zinc Oxide | 1.00% |
| Magnesium Oxide | 0.30% | Magnesium Oxide | 0.30% |
| Chlorophyll | 0.10% | Chlorophyll | 0.10% |

Each of products A and B when mixed appeared physically as a gel delivery format. In several separate trials over 1000 baby calves were treated in the following manner. The gel is orally fed to the stricken calf at 30 cc/calf as a 1-3 time dose depending upon the severity of diarrhea. In nearly all cases after treatment the scours cleared up within days.

As used in the appended claim with respect to the oil blend concentrate, major component refers to at least 40% by weight of the total concentrate being the blended essential oil component; minors include other additives.

A polymeric polyionic organic enhancer can be added to the concentrate and can be the preferred polyethyleneimine (PEI) or can be others such as paramethoxyphenyl ethylmethylamine. The amount can be 0.1 mM to 50 mM, similar to the same amount of the sesquiterpenoids (herein before described).

The polyionic inorganic enhancers if used are preferably polyphosphate enhancers and can include sodium tripolyphosphate, sodium hexametaphosphate, at similar levels.

Other carriers may include minors used for a variety of purposes in various topicals, pills, gelatins, etc. and can include small amounts of Apple Powder, Citrus Pectins, Arabic Gum, Ascorbic Acid, Beeswax, Betaine Hydrochloride, Biotin, Calcium Carbonate (Thermocal), Canola Oil, Cetyl Alcohol, Choline Chloride, Citric Acid, Cobalt Carbonate, Copper Sulfate, Corn Starch, Dextrose, Dry Sweet Orange Flavoring, Flaxseed Oil, Folic Acid, Glycine, Lanolin, Lavendar Oil, Lemon Powder, Lipase DS, Maltodextrin, Manganese Sulfate, Magnesium Chloride, Magnesium Oxide, Malic Acid, Niacin, Olive Oil, Pantothenic Acid, Potassium Chloride, Potassium Sulfate, Polysorbate, Propylene Glycol, Purple Pigment, Pyridoxine HCL, Riboflavin, Seaweed Meal, Probiotics/Bacteria, Selenium, Silicon 505, Silicon Dioxide, Sodium Acetate, Sodium Chloride, Sodium Citrate, Sodium Propinate, Sodium Silica Aluminate—MS, Spearmint Oil, SST (Activated Charcoal), Steryl Alcohol, Thiamine, Vaseline, Vitamin A, Vitamin B12 600 mg, Vitamin D3 500, Vitamin E, Vitamin K, Water, and Zinc Sulfate.

Applicants have also discovered that further anti-microbial property enhancement is achieved if from 0.01% by weight to 10% by weight, preferably 0.05% by weight to 5.0% by weight of the concentrate is an organic acid anti-microbial selected from the group of acetic, butyric, citric, lactic and fumaric.

Testing of the combination of oils at Iowa State University during the year 2006/2007 revealed that the combination of oils was more effective from an antimicrobial standpoint than the single oils alone. Preferred was the oil blend previously described as the first oil blend and the second oil blend. These oils in combination with various carriers in concentrate form may be used to add to a variety of veterinarian and human use finished product compositions; and, those can include in delivery format pills, gelatin capsules, skin topicals, gels, creams, liquid rub-ons, powders, shampoos, G.I. tract medicines, etc.

To make a final finished product the concentrate containing the plant essential oil blend is added to the remaining ingredients of the finished product to provide from 0.05% to about 25% by weight of the overall finished product, preferably from 0.5% to 10% by weight of the finished product, and most preferably from 0.5% to 5% by weight of the finished product.

The combination of essential oils, and the enhancers offer many advantages for the anti-microbial composition of finished products. For one, they are not widely rejected by treatment animals because they contain natural scents of the plants from which they are derived, and the animals are used to these scents. Another advantage is the enhanced effectiveness as an anti-microbial. A third is the ease of processability with other finished product ingredients. And a still further advantage is the wide variety of delivery formats that can be presented.

It therefore can be seen that the invention accomplishes at least all of its stated objectives.

What is claimed is:

1. A method of increasing the cellular uptake of plant essential oils in cells comprising:
   exposing the cells to a combination of:
   a) an antimicrobial effective amount of at least two essential oils including oregano oil and cinnamon oil; and
   b) an effective amount of cellular uptake enhancer selected from the group consisting of polyorganic ionic enhancer, and polyinorganic ionic enhancers.

2. The method of claim 1 wherein the combination of plant essential oils further includes thymol.

3. The method of claim 1 wherein the combination of essential oils and enhancer are microencapsulated in a multi-walled capsule.

4. The method of claim 3 wherein the components of the multi-walled capsule are chosen based upon the specific region of the gastrointestinal tract in which they are desired to dissolve.

* * * * *